United States Patent [19]

Plan et al.

[11] 4,169,829

[45] Oct. 2, 1979

[54] PROCESS FOR THE PREPARATION OF PURIFIED ALBUMIN AND ALBUMIN OBTAINED BY SAID PROCESS

[75] Inventors: Robert Plan, Lyons; Jacques Liautaud, Limonest; Marie-France Makula, Lyons; Paule Gattel, Caluire; Jean Pla, Sainte-Foy-lès-Lyon; André Debrus, Lyons, all of France

[73] Assignee: Institut Merieux, Paris, France

[21] Appl. No.: 838,054

[22] Filed: Sep. 30, 1977

Related U.S. Application Data

[63] Continuation of Ser. No. 376,202, Jul. 3, 1973, abandoned.

[30] Foreign Application Priority Data

Jul. 5, 1972 [FR] France ............ 72.24310

[51] Int. Cl.[2] ............ C07G 7/00

[52] U.S. Cl. ............ 260/122; 260/121

[58] Field of Search ............ 260/112 B, 121, 122

[56] References Cited

U.S. PATENT DOCUMENTS 3,497,492 2/1970 Buck ............ 260/122

OTHER PUBLICATIONS

Petrova, Chem. Abs. vol. 75, No. 33006h, 1971.

Mirskaya, Chem. Abs. vol. 72, No. 118424f, 1970.

Kiselev, Chem. Abs. vol. 71, No. 121423q, 1969.

*Primary Examiner*—Paul R. Michl

*Attorney, Agent, or Firm*—Cushman, Darby & Cushman

[57] ABSTRACT

Purified albumin is prepared from frozen placenta, placental blood or other hemolyzed blood by the steps of eliminating hemoglobin, eliminating enzymes and eliminating group substances.

16 Claims, No Drawings

PROCESS FOR THE PREPARATION OF PURIFIED ALBUMIN AND ALBUMIN OBTAINED BY SAID PROCESS

This is a continuation of application Ser. No. 376,202 filed July 3, 1973, now abandoned.

The present invention relates to a process for preparing purified albumin, particularly human albumin, and to the purified albumin obtained by said process.

A certain number of processes for purifying human or animal albumin are already known, using plasma solutions from various sources. None of these processes, however, has made it possible, at least at a sufficiently economic cost to produce large quantities of undenatured, purified albumin, for example human albumin, especially where the raw material used, such as frozen placenta, placental blood, or any hemolyzed blood, contains numerous impurities since such impurities, until now, have not been eliminated to the degree desired.

The present invention however provides a process for preparing purified albumin, especially human albumin, which is both simple and economical and which makes it possible to prepare, industrially, large quantities of highly purified albumin from the most common sources, such as frozen placentas or hemolyzed blood.

The purified albumin obtained in accordance with this invention, when it is of human origin, can be used in the preparation of protein solutions usable as transfusion fluids, for example, in the treatment of shock, or in situations where there is a dangerous reduction in the quantity of circulating blood. The purified albumin obtained by the process according to the present invention is particularly well received by the receiver organism and does not cause those reactions which often occur with the albumin preparations used until now and prepared from such raw materials.

Thus, the present invention has for an object a process for preparing purified albumin, especially human albumin, using placentas, placental blood or any hemolyzed blood, said process comprising the steps of (a) eliminating the hemoglobin, (b) eliminating enzymes, such as the alkaline phosphatases by precipitation of the proteins by means of an acid such as trichloroacetic acid or polyphosphoric acid and (c) eliminating group substances.

The elimination of the hemoglobin can advantageously be carried out in the presence of an ethanol concentration less than 60%, with addition of a halogenated hydrocarbon such as chloroform. It can, however, also be carried out by the addition of a halogenated hydrocarbon, without alcohol or by other known processes.

The elimination of enzymes, such as the phosphatases, is carried out preferably after the hemoglobin elimination stage and preferably carried out in the presence of an ethanol concentration lower than 60%, with addition of trichloroacetic acid. The acid concentration can be between $3\times10^{-2}$ and $10\times10^{-2}$ M/liter, the acid being added to the protein solution at a temperature lower than 0° C. and, preferably, between $-5°$ and $-10°$ C., until essentially total precipitation of the proteins is achieved.

In addition to eliminating enzymes, this stage also makes it possible to concentrate an appreciable quantity of the albumin in solution because the albumin precipitates.

In certain cases, it is possible to replace the precipitation with the trichloroacetic acid by a precipitation with a polyphosphoric acid.

The elimination group substances is carried out preferably with an ethanol concentration greater than 55%, for example, about 75%, with a protein concentration preferably lower than or equal to 10 g/liter and by adding trichloroacetic acid to the solution at a temperature lower than 0°, for example, between $-5°$ and $-10°$ C. The quantity of trichloroacetic acid can advantageously be from $5\times10^{-2}$ to $8\times10^{-2}$ M/liter. The precipitate obtained is discarded, thereby eliminating the group substances.

This group substances elimination stage also makes it possible to remove alkaline phosphatases, so that the preceding stage of elimination of phosphatases can, if desired, be omitted and replaced by a simple protein concentration operation.

In a particularly advantageous embodiment, the process according to the present invention can additionally include, after the above-mentioned procedures, a stage consisting in the elimination of the last possible traces of heterogeneous proteins, as well as the denatured fraction of the albumin by thermocoagulation in the presence of a short chain fatty acid, such as caprylic acid.

Advantageously, thermocoagulation is carried out after having adjusted, if necessary, the protein concentration to a value at least equal to 50 g/liter, the pH being established at a value of between 4.5 and 5.5, at a temperature of between 52° C. and 64° C., and preferably between 56° C. and 60° C. Sodium caprylate is used at a concentration, preferably, between 2 and 12 g/liter according to the protein concentration. Moreover thermocoagulation is generally carried out for a period of time greater than about ½ hour.

In accordance with a further embodiment of the present invention, a clarification stage can be included before elimination of the group substances stage. This clarification operation is carried out by the adding to the solution being treated a silica gel such as aerosil, centrifuging the same and the collected precipitate being discarded. The aerosil concentration can advantageously be about 0.2% by weight of the solution being treated.

The present invention also has for an object the albumin prepared in accordance with the process described above, which albumin has properties which are almost identical to those of natural organic albumin. Thus the albumin produced in accordance with the present invention can be used for the treatment of human infirmities in, for example, the form of plasma.

The invention will now be described in greater detail by the following example.

Beginning with approximately seven tons of placenta, the supernatant of the globulins is prepared by precipitation of the globulins with ethanol in a conventional manner.

1. Elimination of Hemoglobin

To the alcoholic supernatant containing about 25% ethanol and containing approximately 58 g of protein per kg of placenta, chloroform is added so that the total volume of about 17,000 liters contains 0.6% chloroform. The pH is then adjusted to a value of between 6.0 and 6.1.

The supernatant is maintained under these conditions, at a temperature of about 24° C. whereby a precipitate is formed which is then separated and discarded.

The volume of supernatant is thus reduced to approximately 16,000 liters and the protein yield is about 8 g/kilo. The greatest part of the hemoglobin content has thus been eliminated.

2. Elimination of the Enzymes

To the supernatant of 16,000 liters obtained above, containing about 25% ethanol and after lowering the temperature thereof to −8° C., trichloroacetic acid is added to obtain a concentration of $4.2\times10^{-2}$ M/liter. The amount of proteins is about 4 g/l.

There is thus obtained a precipitate of about 1000 kg, while the supernatant having a volume of about 15,000 liters, is discarded. For this purpose, hermetic ejection centrifuges are preferably used with continuous ejection of the precipitate. Thus the alkaline phosphatases and other enzymes, such as transaminases, are eliminated or denatured.

The resulting precipitate is then redissolved in dilute NaOH to a neutral pH and the volume is adjusted to 1300 liters with water.

3. Clarification

To this redissolved precipitate, there is added silica powder (aerosil) to obtain an aerosil concentration of about 0.2%. Thus, a precipitate is formed of about 50 kg which is rejected by centrifugation. The clarified supernatant solution corresponds to a protein yield of about 6.5 g/kg.

4. Elimination of group Substances

Group substances are principally formed of polysaccharides of walls of erythrocytes which are dissolved during hemolysis and which must be eliminated.

The clarified solution from step 3 above is diluted with a mixture of ethanol and trichloroacetic acid, the final proportion of alcohol being about 75% and the portion of trichloroacetic acid being about $8\times10^{-2}$ M/liter. The protein content is about 10 g/liter. The temperature being maintained at about −7° C., a precipitate of about 10 kg is formed which is rejected, and the group substances are eliminated. This stage also completes the elimination of possible residual enzymes.

The supernatant which contains about 8 g/l of proteins is then filtered and the pH is adjusted to a value of between 6.5 and 7, the temperatures always being maintained between −5° and −10° C. The albumin precipitate which is thus formed in then centrifuged, yielding about 140 kg of precipitate. The supernatant is discarded.

5. Purification of the Albumin

The precipitate resulting from step 4 is redissolved in water to provide a volume of about 280 liters, the protein yield being 5 g/kg.

After dialysis against distilled water to eliminate the alcohol, the level of protein is adjusted to 20 g/liter. Then sodium caprylate, in a concentration of $2.41\times10^{-2}$ M/liter (4 g/liter) is added to solution, and the pH is adjusted to a value of between 5.0 and 5.05, for example, with an acetic buffering solution.

This solution is kept at 60° C. for about 1 hour.

The remaining proteins, except the albumin, are thus coagulated and are rejected in a precipitate with the last traces of hemoglobin as well as the denatured fraction of albumin. Essentially only the pure albumin remains in solution.

The resulting supernatant is then brought to about 1750 liters and is then filtered. The diluted albumin solution is then concentrated by adjusting 40% ethanol to a pH of between 4.8 and 4.9, at a temperature of about −8° C. A precipitate is then formed which is collected, then redissolved, this new solution then being dialyzed and then treated on alumina gel. A concentration in vacuo is then carried out followed by a sterilizing filtration to provide about 95 liters of an essentially pure concentrated solution of albumin of about 200 g/liter. At this final stage, the protein yield is about 2.7 g/kg. The coloration of the solution is comparable to that of most good solutions of plasmatic origin.

The invention described by means of this example is, of course, capable of being the subject of numerous variations. Thus, the order in which these steps are carried out may be modified.

The human albumin thus prepared is free of group substances and a placental alkaline phosphatase and does not have a hypotensive effect on the perfused dog. Its low amount of hemoglobin makes it comparable to and even superior to most albumins of plasmatic origin.

This albumin can be used for therapeutic purposes in man without harm and meets all the criteria established for albumin control.

What is claimed is:

1. A process for preparing purified human albumin essentially free of group substances and alkaline phosphatases from a starting impure albumin solution obtained from placental blood or hemolyzed venous blood from which solution hemoglobins and globulins have been eliminated, which comprises adding ethanol to said impure albumin solution in an amount sufficient so that the ethanol concentration is greater than 55%, adding trichloroacetic acid to said ethanol-containing solution in an amount sufficient so that the concentration therein is from $5\times10^{-2}$ to $8\times10^{-2}$ M/liter and adjusting the temperature to lower than 0° C. whereby a precipitate containing said group substances and alkaline phosphatases is formed and removing the thus formed precipitate.

2. The process of claim 1 wherein the ethanol-containing solution to which said trichloroacetic acid is added contains proteins in an amount lower than or equal to 10 g/l and the ethanol concentration is about 75%.

3. The process of claim 1 wherein trichloroacetic acid is added at a temperature of −5° to −10° C.

4. The process of claim 1 wherein the starting impure albumin solution is a solution of placental blood from which globulins have been eliminated by precipitation with the addition of ethanol at a concentration of 25% and by removal therefrom of the resulting precipitated globulins.

5. The process of claim 4 wherein said starting impure albumin solution is said solution of placental blood from which a significant amount of the hemoglobin content thereof has also been eliminated subsequent to the elimination of said globulins and prior to the removal of said group substances and alkaline phosphatases by adding to said essentially globulin-free solution sufficient chloroform to precipitate a major portion of said hemoglobin, adjusting the pH thereof to between 6.0 and 6.1, removing the precipitated hemoglobin and thereafter concentrating the remainder so that the protein content therein is lower than or equal to 10 g/l.

6. The process of claim 5 wherein the step of concentrating the said remainder subsequent to the removal of the said precipitated hemoglobin consists of cooling the remainder to a temperature between −5° and −10° C., adding sufficient trichloroacetic acid or polyphosphoric acid thereto to form an albumin-containing precipitate, recovering said albumin-containing precipitate, and dissolving said recovered albumin-containing precipitate in an alkaline solution at neutral pH, the amount of alkaline solution used being such that the concentration of proteins therein does not exceed 10 g/l.

7. The process of claim 6 which includes subsequent to dissolving said recovered albumin-containing precipitate in said alkaline solution, adding thereto silica powder in an amount sufficient to form a precipitate and thereafter removing said precipitate.

8. The process of claim 1 which includes subsequent to the removal of said group substances and alkaline phosphatases, thermocoagulating the remainder in the presence of caprylate in an amount sufficient to remove the last traces of hemoglobin.

9. The process of claim 8 wherein the caprylate is sodium caprylate.

10. Process according to claim 8 wherein thermocoagulation is carried out after having adjusted the protein concentration to a value not greater than 50 g/liter, and at a pH between 4.5 and 5.5 and at a temperature between 52° C. and 64° C.

11. The process of claim 10 wherein the thermocoagulation temperature is between 56°-60° C.

12. Process according to claim 9 wherein the sodium caprylate concentration is between 2 and 12 g/liter.

13. Process according to claim 8 wherein thermocoagulation is carried out for a period greater than ½ hour.

14. A process for preparing purified human albumin essentially free of group substances and alkaline phosphatases from a starting impure albumin solution obtained from placental blood or hemolyzed venous blood comprising the steps of (a) adding ethanol to said placental blood or hemolyzed venous blood in an amount sufficient so that the ethanol concentration therein is about 25% whereby a precipitate containing globulins is formed and a supernatant containing ethanol in a concentration of about 25% hemoglobins, albumin, group substances and alkaline phosphates, is formed, (b) adding chloroform to said supernatant from (a), adjusting the pH thereof to a value between 6.0 and 6.1 and maintaining said supernatant at a temperature of about 24° C. whereby a precipitate containing said hemoglobins is formed and discarded and a supernatant containing about 25% ethanol, albumin, group substances and alkaline phosphatases is formed, (c) adding trichloroacetic acid to the supernatant from (b) containing ethanol at a concentration of about 25% in an amount sufficient so that the concentration of said trichloroacetic acid therein is about $3\times10^{-2}$ to $10\times10^{-2}$ M/liter and adjusting the temperature to about −5° to −10° C. whereby a supernatant containing said alkaline phosphatases is formed and discarded and a precipitate containing said albumin and group substances is formed, (d) dissolving said precipitate from (c) in dilute NaOH to a neutral pH, (e) adding to the solution resulting from (d) silica to clarify the same whereby a precipitate is formed and discarded and a clarified supernatant containing said albumin and said group substances is formed, (f) adding to the clarified supernatant from (e) a mixture of ethanol and trichloroacetic acid the concentration of ethanol being about 75% and the concentration of trichloroacetic acid being about $5\times10^{-2}$ to $8\times10^{-2}$ M/liter at a temperature between −5° to −10° C. whereby a precipitate containing said group substances is formed and discarded together with any residual alkaline phosphatases, and a supernatant containing said albumin is formed, (g) adjusting the pH of the supernatant from (f) to a value between 6.5 and 7, at a temperature between −5° and −10° C. whereby a supernatant is formed and discarded and a precipitate containing said albumin is formed.

15. A process for preparing purified human albumin essentially free of group substances and alkaline phosphatases from a starting impure albumin solution obtained from placental blood or hemolyzed venous blood comprising the steps of (a) adding sufficient ethanol to said placental blood or hemolyzed venous blood so that the ethanol concentration therein is about 25% whereby a precipitate containing globulins is formed and discarded and a supernatant containing about 25% ethanol, hemoglobins, albumin, alkaline phosphatases and group substances if formed, (b) adding to the supernatant from (a) chloroform and adjusting the pH to a value between 6.0 and 6.1 while maintaining the temperature of about 24° C. whereby a precipitate containing said hemoglobins is formed and discarded and a supernatant containing about 25% ethanol, albumin, group substances and alkaline phosphatases is formed, (c) adding to the supernatant from (b) trichloroacetic acid to provide a concentration therein of about $3\times10^{-2}$ to $10\times10^{-2}$ M/liter and adjusting the temperature to about −5° to −10° C. whereby a supernatant containing said alkaline phosphatases is formed and discarded and a precipitate containing said albumin and group substances is formed, and (d) adding to the precipitate from (c) a mixture of ethanol and trichloroacetic acid, the concentration of ethanol being about 75% and the concentration of trichloroacetic acid being about $5\times10^{-2}$ to $8\times10^{-2}$ M/liter and maintaining the temperature between −5° and −10° C. whereby a precipitate containing said group substances is formed and discarded together with any residual alkaline phosphatases and a supernatant containing said albumin is formed.

16. Purified albumin and human placental origin free of group substances and alkaline phosphatases.

* * * * *

UNITED STATES PATENT AND TRADEMARK OFFICE

CERTIFICATE OF CORRECTION

PATENT NO. : 4,169,829

DATED : October 2, 1979

INVENTOR(S) : Robert Plan, Jacques Liautaud, Marie-France Makula Paule Gattel, Jean Pla, and Andre Debrus It is certified that error appears in the above-identified patent and that said Letters Patent are hereby corrected as shown below:

In claim 16, Col. 6, line 60, change "and" to --of--.

Signed and Sealed this

*Tenth* Day of *June 1980*

[SEAL]

*Attest:*

SIDNEY A. DIAMOND

*Attesting Officer* *Commissioner of Patents and Trademarl*